US007070769B2

(12) United States Patent
Ascione et al.

(10) Patent No.: US 7,070,769 B2
(45) Date of Patent: Jul. 4, 2006

(54) COMPOSITIONS COMPRISING AT LEAST TWO ANIONIC ASSOCIATIVE POLYMERS AND THEIR USE FOR STABILIZATION OF AN OXIDIZING SOLUTION

(75) Inventors: Jean-Marc Ascione, New York, NY (US); Michael De George, Toms River, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/809,009

(22) Filed: Mar. 16, 2001

(65) Prior Publication Data

US 2002/0152556 A1 Oct. 24, 2002

Related U.S. Application Data

(60) Provisional application No. 60/268,905, filed on Feb. 16, 2001.

(51) Int. Cl.
*A61K 7/135* (2006.01)

(52) U.S. Cl. .................. 424/62; 424/70.11; 424/70.16; 132/202; 132/208; 252/186.25; 252/186.41

(58) Field of Classification Search .................... 8/405, 8/406, 409, 410, 412, 416, 558, 554, 557; 424/62, 70.11, 70.16; 132/202, 208; 252/186.25, 252/186.41
See application file for complete search history.

(56) References Cited

U.S. PATENT DOCUMENTS

| 4,776,855 | A | 10/1988 | Pohl et al. ...................... 8/406 |
| 4,806,345 | A | 2/1989 | Bhattacharyya ............... 424/70 |
| RE33,786 | E | 1/1992 | Pohl et al. ...................... 8/406 |
| 5,376,146 | A | 12/1994 | Casperson et al. ............. 8/408 |
| 5,393,305 | A | 2/1995 | Cohen et al. ................... 8/406 |
| 5,830,447 | A | * 11/1998 | Hutchins et al. ......... 424/70.12 |
| 5,976,195 | A | * 11/1999 | de la Mettrie et al. ............ 8/11 |
| 5,989,295 | A | * 11/1999 | de la Mettrie et al. ......... 8/406 |

FOREIGN PATENT DOCUMENTS

| EP | 0852943 A | 7/1998 |
| EP | 0875241 A | 11/1998 |
| WO | WO 00 21494 A | 4/2000 |
| WO | WO 02 065996 A | 8/2002 |

OTHER PUBLICATIONS

XP- 000934522 "Application of Acrylates/Methacrylates/Beheneth-25 Methacrylate Copolymer (Aculyn 28) as a Thickener and Suspending Agent in Cosmetic Formulations and as a Polymeric Emulsifier" (Dec.-1999).*
European Search Report mailed Feb. 28, 2003 for PCT/US02/22076.
"Application of Acrylates/Methacrylates/Beheneth-25 methacrylate copolymer (aculyn 28) as a thickener and suspending agent in cosmetic formulations and as a polymeric emulsifier" Research Disclosure, Kenneth Mason Publications, Hampshire, GB, vol. 428, (Dec. 1999), pp. 1553-1554, AN42801, XP009000073 ISSN: 0374-4353.

* cited by examiner

*Primary Examiner*—Eisa Elhilo
(74) *Attorney, Agent, or Firm*—Finnegan Henderson Farabow Garrett & Dunner, L.L.P.

(57) ABSTRACT

Compositions comprising (i) at least one anionic associative polymer comprising at least one carboxylic acid group and at least one ester derived from a fatty alcohol and a carboxylic acid; (ii) at least one additional anionic associative polymer comprising at least one carboxylic acid group and at least one ester derived from an alkoxylated fatty alcohol and a carboxylic acid; and (iii) at least one oxidizing agent, and processes using the same for providing physical stability to an oxidizing composition, and in hair treatment compositions.

29 Claims, No Drawings

COMPOSITIONS COMPRISING AT LEAST TWO ANIONIC ASSOCIATIVE POLYMERS AND THEIR USE FOR STABILIZATION OF AN OXIDIZING SOLUTION

This application is based upon and claims the benefit of priority of U.S. provisional application No. 60/268,905, filed Feb. 16, 2001, the disclosure of which is incorporated herein by reference.

The present invention relates to compositions comprising (i) at least one anionic associative polymer comprising at least one carboxylic acid group and at least one ester derived from a fatty alcohol and a carboxylic acid; (ii) at least one additional anionic associative polymer comprising at least one carboxylic acid group and at least one ester derived from an alkoxylated fatty alcohol and a carboxylic acid; and (iii) at least one oxidizing agent.

The inventive compositions may provide physical stability to an oxidizing composition. The oxidizing compositions of the invention may be useful in, for example, a process chosen from dyeing, bleaching, relaxing, and permanent waving of keratinous fibers. The invention also provides a process for providing physical stability to an oxidizing composition.

It is very popular to treat keratinous fibers, particularly human hair, with various hair treatments such as dyeing, bleaching, permanent waving, or relaxing/straightening treatments. Normally these chemical treatments involve the use of an oxidizing composition.

Hair fiber, a keratinous material, is comprised of proteins (polypeptides) many of which are bonded together by disulfide bonds (—S—S—). A disulfide bond may be formed from the reaction of two sulfhydryl groups (—SH), one on each of two cysteine residues, which results in the formation of a cystine residue. While there may be other types of bonds which occur between the polypeptides in hair fibers, such as salt (ionic) bonds, the permanent curling or the shape of the hair is essentially dependent on the disulfide bonds of cystine residues.

As a result, relaxing or straightening of hair can be achieved by disrupting the disulfide bonds of the hair fibers with an alkaline or a reducing agent. The chemical disruption of disulfide bonds by an alkaline agent is usually combined with mechanical straightening of the hair, such as combing, and straightening generally occurs due to changes in the relative positions of opposing polypeptide chains within the hair fiber. The reaction is generally terminated by rinsing and/or the application of a neutralizing composition, such as an oxidizing composition.

Another example of a chemical treatment that utilizes an oxidizing composition is permanent waving. Hair that has been treated with a reducing agent to break the hair's disulfide bonds can be neutralized with an oxidizing composition to stop the reducing process so the bonds can re-form to provide wavy or curly hair.

Hair dyes also may utilize an oxidizing composition, such as hydrogen peroxide, in combination with a dye-containing solution to provide an oxygen source for lifting natural pigment and/or for synthetic dye oxidation.

When formulating an oxidizing composition, however, one faces the challenges of chemical stability of the oxidizing agent and physical stability of the oxidizing composition. The physical stability, for example, may be important to ensure a homogenous oxidizing activity. A non-homogeneous oxidizing composition may lead to variation in oxidizing activity that may result in problems with safety and/or performance, and/or variation in viscosity that may also result in performance issues.

Thus, there is a need for oxidizing compositions that are physically stable and may be used in conjunction with popular chemical treatments for keratinous fibers. The inventors have found that the use of at least one anionic associative polymer and at least one additional anionic associative polymer in an oxidizing composition may result in a physically stable composition.

In one embodiment, the invention provides a composition comprising (i) at least one anionic associative polymer comprising at least one carboxylic acid group and at least one ester derived from a fatty alcohol and a carboxylic acid; and (ii) at least one additional anionic associative polymer comprising at least one carboxylic acid group and at least one ester derived from an alkoxylated fatty alcohol and a carboxylic acid. The composition further comprises at least one oxidizing agent. In a further embodiment, the at least one anionic associative polymer and the at least one additional anionic associative polymer are present in a combined amount effective to stabilize the composition. As used herein, "at least one" means one or more and thus includes individual components as well as mixtures/combinations.

The invention also provides a method for providing physical stability to an oxidizing composition comprising including in the oxidizing composition (i) at least one anionic associative polymer comprising at least one carboxylic acid group and at least one ester derived from a fatty alcohol and a carboxylic acid; and (ii) at least one additional anionic associative polymer comprising at least one carboxylic acid group and at least one ester derived from an alkoxylated fatty alcohol and a carboxylic acid. The anionic associative polymer and the additional anionic associative polymer are present in a combined amount effective to provide stability to the oxidizing composition.

The present invention also discloses a method for treating keratinous fibers comprising applying to said keratinous fibers at least one treatment composition comprising an oxidizing composition, wherein said oxidizing composition comprises (i) at least one anionic associative polymer comprising at least one carboxylic acid group and at least one ester derived from a fatty alcohol and a carboxylic acid; (ii) at least one additional anionic associative polymer comprising at least one carboxylic acid group and at least one ester derived from an alkoxylated fatty alcohol and a carboxylic acid; and (iii) at least one oxidizing agent.

Yet another subject of the present invention is a multi-compartment kit for the chemical treatment of keratinous fibers, where the kit has at least two separate compartments. The first compartment contains an oxidizing composition comprising (i) at least one anionic associative polymer comprising at least one carboxylic acid group and at least one ester derived from a fatty alcohol and a carboxylic acid; and (ii) at least one additional anionic associative polymer comprising at least one carboxylic acid group and at least one ester derived from an alkoxylated fatty alcohol and a carboxylic acid. The oxidizing composition further comprises at least one oxidizing agent. The second compartment contains a composition for chemical treatment of the fibers, e.g., dyeing, bleaching, permanent waving, or relaxing.

It is to be understood that both the foregoing general description and the following detailed description are exemplary and explanatory only and are not restrictive of the invention as claimed.

One subject of the invention is an oxidizing composition which may be useful in the chemical treatment of keratinous material, such as, for example, dyeing, bleaching, relaxing, and permanent waving of keratinous fibers. In one embodiment, the compositions of the invention are physically stable.

As used herein, "physical stability" is tested by placing the composition in a controlled environment chamber for 8 weeks at 45° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for phase separation. A composition is considered to lack physical stability if separation of the phases of a composition is observed by the human eye. Accordingly, a composition is considered "physically stable" if no phase separation is observed at 8 weeks in the above test. Thus, as used herein, "stabilization" means making a composition "physically stable".

The at least one anionic associative polymer of the present invention comprises at least one carboxylic acid group and at least one ester derived from a fatty alcohol and a carboxylic acid. The fatty alcohol, for example, may be chosen from $C_8$ to $C_{36}$ fatty alcohols.

In a further embodiment, the at least one anionic associative polymer may be chosen from copolymers derived from (i) at least one monomer chosen from $C_{10}$–$C_{30}$ alkyl acrylates and (ii) at least one monomer comprising at least one carboxylic acid group. The at least one anionic associative polymer may further comprise at least one unit comprising at least one ester chosen from esters derived from acrylic acid and esters derived from methacrylic acid. The at least one monomer comprising at least one carboxylic acid group, in one embodiment, may be chosen from acrylic acid and methacrylic acid. In a further embodiment, the at least one anionic associative polymer may be crosslinked with at least one allyl ether chosen from allyl ethers of sucrose and allyl ethers of pentaerythritol.

Non-limiting examples of at the least one anionic associative polymer which may be used in the composition according to the present invention include Acrylates/C10–30 Alkyl Acrylate Crosspolymers, which are sold by Goodrich under the names Carbopol 1342, Carbopol 1382, Carbopol ETD 2020, Pemulen TR-1, and Pemulen TR-2.

The at least one additional anionic associative polymer of the present invention comprises at least one carboxylic acid group and at least one ester derived from an alkoxylated fatty alcohol and a carboxylic acid. The alkoxylated fatty alcohol may be chosen, for example, from polyethylene glycol ethers.

In one embodiment, the at least one additional anionic associative polymer may be chosen from copolymers derived from (i) at least one monomer comprising at least one ester derived from a carboxylic acid and a polyethylene glycol ether and (ii) at least one monomer comprising at least one carboxylic acid group. The at least one monomer comprising at least one carboxylic acid group, in one embodiment, may be chosen from acrylic acid and methacrylic acid. The at least one additional anionic associative polymer may further comprise at least one unit comprising at least one ester chosen from esters derived from acrylic acid and a polyethylene glycol ether and esters derived from methacrylic acid and a polyethylene glycol ether. The polyethylene glycol ether, for example, may be chosen from polyethylene glycol ethers of at least one alcohol chosen from stearyl alcohol, lauryl alcohol, nondecanol, arachidyl alcohol, heneicosanol, behenyl alcohol, tricosanol, triacontanol, and hentriacontanol.

Non-limiting examples of the at least one additional anionic associative polymer which may be used in the composition according to the present invention include Acrylates/ Steareth-20 Methacrylate Copolymer, which is sold by Rohm & Haas under the name Aculyn 22; and Acrylates/Beheneth-25 Methacrylate Copolymer, which is sold by Rohm & Haas under the name Aculyn 28.

As described above, in one embodiment, the at least one anionic associative polymer and the at least one additional anionic associative polymer may be present in a combined amount effective to stabilize the composition. While the presence of only one of the anionic associative polymers may be enough to physically stabilize an oxidizing composition, the result is often too high a concentration of the particular anionic associative polymer and thus a composition that is too viscous for the application envisaged. Furthermore, a very viscous composition may only slow down phase separation as opposed to substantially stabilizing the composition. However, the use of both the at least one anionic associative polymer and the at least one additional anionic associative polymer of the present invention, may result in a physically stable composition at a lower total concentration of anionic associative polymers as compared to the concentration of a single anionic associative polymer that would be required to result in a physically stable composition.

One of skill in the art, armed with the physical stability test described herein, may chose the concentration of the at least one anionic associative polymer and the concentration of at least one additional anionic associative polymer based on the physical stability desired and the application envisaged. The skilled artisan may also use the physical stability test to choose the combination of associative polymers which results in the desired stability for the application.

In one embodiment, the at least one anionic associative polymer may be present in a composition in an amount generally ranging from 0.01% to 2.50% by weight relative to the total weight of the composition. The at least one additional anionic associative polymer may be present in a composition, for example, in an amount generally ranging from 0.01% to 5.00% by weight relative to the total weight of the composition.

In one embodiment, the at least one oxidizing agent of the present invention may be chosen from any oxidizing agent that is known in the art for use with the chemical treatment of keratinous materials. For example, the at least one oxidizing agent may be chosen from hydrogen peroxides, bromate salts, percarbonate salts, perborate salts and enzymes. In one embodiment, the at least one oxidizing agent is hydrogen peroxide. In another embodiment, the at least one oxidizing agent may be present in a composition in an amount generally ranging from 0.1% to 20.0% by weight relative to the total weight of the composition.

The composition of the present invention can also contain various adjuvants conventionally used in compositions for treating the hair, such as, but not limited to, anionic surfactants, cationic surfactants, nonionic surfactants, and amphoteric surfactants; anionic polymers other than the anionic polymers discussed above, cationic polymers, nonionic polymers, and amphoteric polymers; inorganic thickeners and organic thickeners; conditioners; chelating agents, antioxidants; stabilizing agents; propellants; sequestering agents; emollients; humectants; fragrances; acidifying and basifying agents; chelating agents, moisturizing agents; vitamins; essential fatty acids; proteins and protein derivatives; dyes; alkaline agents; reducing agents; preservatives; and opacifiers.

Needless to say, a person skilled in the art will take care to select optional adjuvants such that the advantageous properties intrinsically associated with the invention are not, or are not substantially, adversely affected by the addition(s) envisaged.

The compositions of the present invention may be in a form, for example, chosen from an aqueous emulsion, a suspension, a dispersion, a gel, a spray, an aerosol foam, a cream, a lotion, a solution, a paste, and a hydroalcoholic lotion.

The invention also provides a method for providing physical stability to an oxidizing composition comprising including in the oxidizing composition (i) at least one anionic associative polymer comprising at least one carboxylic acid group and at least one ester derived from a fatty alcohol and a carboxylic acid; and (ii) at least one additional anionic associative polymer comprising at least one carboxylic acid group and at least one ester derived from an alkoxylated fatty alcohol and a carboxylic acid. The at least one anionic associative polymer and the at least one additional anionic associative polymer are present in a combined amount effective to provide physical stability to the oxidizing composition.

Another subject of the present invention is a method for treating keratinous fibers comprising applying to said keratinous fibers at least one treatment composition comprising an oxidizing composition, wherein said oxidizing composition comprises (i) at least one anionic associative polymer comprising at least one carboxylic acid group and at least one ester derived from a fatty alcohol and a carboxylic acid; (ii) at least one additional anionic associative polymer comprising at least one carboxylic acid group and at least one ester derived from an alkoxylated fatty alcohol and a carboxylic acid; and (iii) at least one oxidizing agent. In one embodiment, the at least one treatment composition is chosen from a dyeing composition, a bleaching composition, a permanent waving composition, and a relaxing composition.

Yet another subject of the present invention is a multi-compartment kit for the treatment, such as chemical treatment, of keratinous fibers, wherein the kit has at least two separate compartments. The first compartment contains an oxidizing composition comprising (i) at least one anionic associative polymer comprising at least one carboxylic acid group and at least one ester of a fatty alcohol and a carboxylic acid; and (ii) at least one additional anionic associative polymer comprising at least one carboxylic acid group and at least one ester derived from an alkoxylated fatty alcohol and a carboxylic acid. The oxidizing composition further comprises at least one oxidizing agent. The second compartment contains a composition for treatment of the fibers, e.g., dyeing, bleaching, permanent waving, or relaxing.

The example given below, purely by way of illustration and with no limiting nature, will allow the invention to be understood more clearly.

EXAMPLE

Stabilization of an Oxidizing Composition Using a Combination of Anionic Associative Polymers The four following oxidizing compositions, $A_1$, $A_2$, $A_3$, and $A_4$ were prepared. Comparative Composition $A_1$ contained the anionic associative polymer, Acrylates/C10–30 Alkyl Acrylate Crosspolymer (Carbopol ETD 2020), but did not contain the additional anionic associative polymer as described herein. Comparative Composition $A_2$ contained the additional anionic associative polymer, Acrylates/Beheneth-25 Methacrylate Copolymer (Aculyn 28), but did not contain the anionic associative polymer as described herein. Inventive Composition $A_3$ contained the anionic associative polymer, Acrylates/C10–30 Alkyl Acrylate Crosspolymer (Carbopol ETD 2020) and the additional anionic associative polymer, Acrylates/Beheneth-25 Methacrylate Copolymer (Aculyn 28). Inventive Composition $A_4$ contained the anionic associative polymer, Acrylates/C10–30 Alkyl Acrylate Crosspolymer (Carbopol ETD 2020) and the additional anionic associative polymer, Acrylates/Steareth-20 Methacrylate Copolymer (Aculyn 22).

| | CONCENTRATION OF COMPONENT (Percent) | | | |
|---|---|---|---|---|
| COMPONENT (CTFA Name) | Composition $A_1$ (Comparative) | Composition $A_2$ (Comparative) | Composition $A_3$ (Inventive) | Composition $A_4$ (Inventive) |
| HYDROGEN PEROXIDE | 12.00 | 12.00 | 12.00 | 12.00 |
| CETETH-10 | 2.25 | 2.25 | 2.25 | 2.25 |
| ISOCETETH-20 | 1.800 | 1.800 | 1.800 | 1.800 |
| CETETH-2 | 1.125 | 1.125 | 1.125 | 1.125 |
| ACRYLATES/ C10–30 ALKYL ACRYLATE CROSSPOLYMER | 0.6 | — | 0.6 | 0.6 |
| ACRYLATES/ BEHENETH-25 METHACRYLATE COPOLYMER | — | 0.3000 | 0.3000 | — |
| ACRYLATES/ STEARETH-20 METHACRYLATE COPOLYMER | — | — | — | 0.3000 |

-continued

| COMPONENT (CTFA Name) | CONCENTRATION OF COMPONENT (Percent) | | | |
|---|---|---|---|---|
| | Composition $A_1$ (Comparative) | Composition $A_2$ (Comparative) | Composition $A_3$ (Inventive) | Composition $A_4$ (Inventive) |
| PENTASODIUM PENTETATE | 0.0380 | 0.0380 | 0.0380 | 0.0380 |
| PHOSPHORIC ACID | Q.S. pH to 3.5 | Q.S. pH to 3.5 | Q.S. pH to 3.5 | Q.S. pH to 3.5 |
| WATER | Q.S. to 100 | Q.S. to 100 | Q.S. to 100 | Q.S. to 100 |

Results

The visual physical stability of the four oxidizing compositions, $A_1$, $A_2$, $A_3$, and $A_4$, was observed at 45° C. The results are listed below.

| Compositions | Appearance (45° C.) |
|---|---|
| $A_1$ (comparative) | substantial phase separation (5 days) |
| $A_2$ (comparative) | substantial phase separation (24 hrs) |
| $A_3$ (inventive) | no substantial phase separation (8 weeks) |
| $A_4$ (inventive) | no substantial phase separation (8 weeks) |

The results demonstrate that acceptable physical stability was only observed for compositions comprising both at least one anionic associative polymer and at least one additional anionic associative polymer.

What is claimed is:

1. A composition comprising:
   at least one anionic associative polymer chosen from Acrylates/C10–30 Alkyl Acrylate Crosspolymers;
   at least one additional anionic associative polymer chosen from Acrylates/Steareth-20 Methacrylate Copolymers and Acrylates/Beheneth-25 Methacrylate Copolymers; and
   at least one oxidizing agent.

2. The composition according to claim 1, wherein said at least one anionic associative polymer and said at least one additional anionic associative polymer are present in a combined amount effective to stabilize the composition.

3. The composition according to claim 1, wherein said at least anionic associative polymer is present in the composition in an amount ranging from 0.01% to 2.5% by weight relative to the total weight of the composition.

4. The composition according to claim 1, wherein said at least one additional anionic associative polymer is present in the composition in an amount ranging from 0.01% to 5.00% by weight relative to the total weight of the composition.

5. The composition according to claim 1, wherein said at least one oxidizing agent is chosen from hydrogen peroxides, bromate salts, percarbonate salts, perborate salts and enzymes.

6. The composition according to claim 5, wherein said at least one oxidizing agent is hydrogen peroxide.

7. The composition according to claim 1, wherein said at least one oxidizing agent is present in the composition in an amount ranging from 0.1% to 20.0% by weight relative to the total weight of the composition.

8. The composition according to claim 1, further comprising at least one adjuvant chosen from anionic surfactants, cationic surfactants, nonionic surfactants, amphoteric surfactants, anionic polymers different from said at least one anionic associative polymer and different from said at least one additional anionic associative polymer, nonionic polymers, cationic polymers, amphoteric polymers, inorganic thickeners, organic thickeners, antioxidants, stabilizing agents, propellants, sequestering agents, emollients, humectants, fragrances, acidifying agents, basifying agents, chelating agents, moisturizing agents, vitamins, essential fatty acids, proteins, protein derivatives, dyes, alkaline agents, reducing agents, preservatives, and opacifiers.

9. The composition according to claim 1, wherein said composition is in the form of an aqueous emulsion, a suspension, a dispersion, an aerosol foam, a cream, a lotion, a solution, a paste, a gel, a spray, or a hydroalcoholic lotion.

10. A method for providing physical stability to an oxidizing composition comprising:
    including in said oxidizing composition:
       at least one anionic associative polymer chosen from Acrylates/C10–30 Alkyl Acrylate Crosspolymers; and
       at least one additional anionic associative polymer chosen from Acrylates/Steareth-20 Methacrylate Copolymers and Acrylates/Beheneth-25 Methacrylate Copolymers;
    wherein said at least one anionic associative polymer and said at least one additional anionic associative polymer are present in a combined amount effective to provide stability to said oxidizing composition.

11. The method according to claim 10, wherein said at least anionic associative polymer is present in the composition in an amount ranging from 0.01% to 2.5% by weight relative to the total weight of said oxidizing composition.

12. The method according to claim 10, wherein said at least one additional anionic associative polymer is present in the composition in an amount ranging from 0.01% to 5.00% by weight relative to the total weight of said oxidizing composition.

13. The method according to claim 10, wherein said at least one oxidizing agent is chosen from hydrogen peroxides, bromate salts, percarbonate salts, perborate salts and enzymes.

14. The method according to claim 13, wherein said at least one oxidizing agent is hydrogen peroxide.

15. The method according to claim 10, wherein said at least one oxidizing agent is present in the composition in an amount ranging from 0.1% to 20.0% by weight relative to the total weight of said oxidizing composition.

16. The method according to claim 10, wherein said oxidizing composition further comprises at least one adjuvant chosen from anionic surfactants, cationic surfactants, nonionic surfactants, amphoteric surfactants, anionic polymers different from said at least one anionic associative polymer and different from said at least one additional anionic associative polymer, nonionic polymers, cationic polymers, amphoteric polymers, inorganic thickeners, organic thickeners, antioxidants, stabilizing agents, propellants, sequestering agents, emollients, humectants, fragrances, acidifying agents, basifying agents, chelating agents, moisturizing agents, vitamins, essential fatty acids, proteins, protein derivatives, dyes, alkaline agents, reducing agents, preservatives, and opacifiers.

17. The method according to claim 10, wherein said oxidizing composition is in the form of an aqueous emulsion, a suspension, a dispersion, an aerosol foam, a cream, a lotion, a solution, a paste, a gel, a spray, or a hydroalcoholic lotion.

18. A method for treating keratinous fibers comprising applying to said keratinous fibers at least one treatment composition comprising an oxidizing composition, wherein said oxidizing composition comprises:
   at least one anionic associative polymer chosen from Acrylates/C10–30 Alkyl Acrylate Crosspolymers;
   at least one additional anionic associative polymer chosen from Acrylates/Steareth-20 Methacrylate Copolymers and Acrylates/Beheneth-25 Methacrylate Copolymers; and
   at least one oxidizing agent.

19. The method according to claim 18, wherein said at least one treatment composition is chosen from a dyeing composition, a bleaching composition, a permanent waving composition, and a relaxing composition.

20. The method according to claim 18, wherein said at least one anionic associative polymer and said at least one additional anionic associative polymer are present in a combined amount effective to stabilize the at least one treatment composition.

21. The method according to claim 18, wherein said at least anionic associative polymer is present in an amount ranging from 0.01% to 2.5% by weight relative to the total weight of the treatment composition.

22. The method according to claim 18, wherein said at least one additional anionic associative polymer is present in an amount ranging from 0.01% to 5.00% by weight relative to the total weight of the treatment composition.

23. The method according to claim 18, wherein said at least one oxidizing agent is chosen from hydrogen peroxides, bromate salts, percarbonate salts, perborate salts and enzymes.

24. The method according to claim 23, wherein said at least one oxidizing agent is hydrogen peroxide.

25. The method according to claim 18, wherein said at least one oxidizing agent is present in an amount ranging from 0.1% to 20.0% by weight relative to the total weight of the treatment composition.

26. The method according to claim 18, wherein said treatment composition further comprises at least one adjuvant chosen from anionic surfactants, cationic surfactants, nonionic surfactants, amphoteric surfactants, anionic polymers different from said at least one anionic associative polymer and different from said at least one additional anionic associative polymer, nonionic polymers, cationic polymers, amphoteric polymers, inorganic thickeners, organic thickeners, antioxidants, stabilizing agents, propellants, sequestering agents, emollients, humectants, fragrances, acidifying agents, basifying agents, chelating agents, moisturizing agents, vitamins, essential fatty acids, proteins, protein derivatives, dyes, alkaline agents, reducing agents, preservatives, and opacifiers.

27. The method according to claim 18, wherein said treatment composition is in the form of an aqueous emulsion, a suspension, a dispersion, an aerosol foam, a cream, a lotion, a solution, a paste, a gel, a spray, or a hydroalcoholic lotion.

28. A multi-compartment kit for treatment of keratinous fibers, said kit comprising at least two separate compartments, wherein
   a first compartment contains an oxidizing composition comprising:
      at least one anionic associative polymer chosen from Acrylates/C10–30 Alkyl Acrylate Crosspolymers;
      at least one additional anionic associative polymer chosen from Acrylates/Steareth-20 Methacrylate Copolymers and Acrylates/Beheneth-25 Methacrylate Copolymers; and
      at least one oxidizing agent; and
   a second compartment contains a composition for treatment of said keratinous fibers.

29. A multi-compartment kit according to claim 28, wherein said composition for treatment of keratinous fibers is chosen from a dyeing composition, a bleaching composition, a permanent waving composition, and a relaxing composition.

* * * * *

UNITED STATES PATENT AND TRADEMARK OFFICE
CERTIFICATE OF CORRECTION

PATENT NO. : 7,070,769 B2  
APPLICATION NO. : 09/809009  
DATED : July 4, 2006  
INVENTOR(S) : Jean-Marc Ascione et al.

Page 1 of 1

It is certified that error appears in the above-identified patent and that said Letters Patent is hereby corrected as shown below:

Claim 3, col. 7, line 48, "least anionic" should read --least one anionic--.

Claim 11, col. 8, line 45, "least anionic" should read --least one anionic--.

Claim 21, col. 9, line 36, "least anionic" should read --least one anionic--.

Signed and Sealed this

Sixth Day of March, 2007

JON W. DUDAS  
*Director of the United States Patent and Trademark Office*